United States Patent [19]

De Cuellar et al.

[11] Patent Number: 4,828,832

[45] Date of Patent: May 9, 1989

[54] METHOD OF MANUFACTURING A COMPOSITION FOR TREATING SKIN LESIONS

[75] Inventors: Blanca Rosa A. De Cuellar, Mexico City; Luis Armando L. Bello, Cuidad Satelite, both of Mexico

[73] Assignee: Laboratorios Biochemie De Mexico, Col. Granada, Mexico

[21] Appl. No.: 18,760

[22] Filed: Feb. 26, 1987

Related U.S. Application Data

[63] Continuation-in-part of Ser. No. 810,524, Dec. 16, 1985, abandoned, which is a continuation of Ser. No. 530,112, Sep. 7, 1983, abandoned.

[51] Int. Cl.[4] .............................................. A61K 33/38
[52] U.S. Cl. ...................................... 424/618; 514/770
[58] Field of Search ................................ 424/132, 125

[56] References Cited

U.S. PATENT DOCUMENTS

| | | | |
|---|---|---|---|
| 3,639,575 | 2/1972 | Schmocka | 424/78 |
| 3,658,984 | 4/1972 | Kamp | 424/28 |
| 4,163,800 | 8/1979 | Wickett et al. | 424/326 |

OTHER PUBLICATIONS

Handbook of Non Prescription Drugs–5th ed., Pub. Amer. Pharm. Assoc., pp. 271–279 (1977).
B. Helwig: "Moderne Arzneimittel", 5th edition, 1980, p. 584; Wissenschaftliche Verlagsgesellschaft mbH, Stuttgart, DE "Katoxyn", (Wundputer, Puderspray).
Collection of miscellaneous undated and untitled tear sheets, fliers, etc., relating to Katadyn.

Primary Examiner—Leonard Schenkman

[57] ABSTRACT

A method of manufacturing a composition for treating skin lesions made up of metallic silver particles dispersed within a carrier which includes applying the composition to the skin lesion.

13 Claims, No Drawings

METHOD OF MANUFACTURING A COMPOSITION FOR TREATING SKIN LESIONS

This application is a continuation-in-part of application Ser. No. 810,524, filed Dec. 16, 1985, which was a continuation of Ser. No. 530,112, filed Sept. 7, 1983, both abandoned.

BACKGROUND OF THE INVENTION

The invention relates to a method of manufacturing a composition for the treatment of skin lesions and more particularly skin burns.

Various therapeutic methods and agents have been used for the local treatment of burns. Liniments and ointments represent the contribution made by the hordes and tribes to the knowledge of local medication. The great Hypocrites provided an ointment made with bitumen and hog fat. Embross Paree preached the use of onion with salt added, instead of the ink that had been used up until that time. In 1797, Sir John Kentich described a method for the treatment of burns which gave shape to what would later be known as the "exposed method." During the first World War, waxes and paraffins were used profusely replacing picric acid. In 1925, Davidson introduced the use of tannic acid which achieved great popularity until it was discovered that this substance was aggressive to liver cells. During the second World War, the "exposed method" was re-evaluated and put into practice.

At present, silver salts in the form of nitrates are used with furazolidones and antibiotics in the treatment of burns. The silver ion is an effective antiseptic and germicide, and its organic salts, particularly nitrates, are used for this purpose. Silver nitrate is one of the most powerful chemical germicides and is used as a local astringent and germicide. It was formally used in conjunction with tannic acid in treating burns. Strong silver proteins were formed in an attempt to produce a substance which would have the desirable disinfectant properties of silver salts but be free from the objectionable irritant action of the nitrate. These strong silver proteins were formed from a silver salt in colloidal combination with protein matter and were found to possess some disinfectant power. Silver sulfadiazine or silvadene and cerium sulfadiazine are used extensively in hospitals in either a cream or spray form to provide topical antimicrobial action for both major and minor burn wounds.

The germicidal effect of inorganic silver salts in topical application is immediate. The silver ion provokes the precipitation of proteins in cells and tissues, altering the metabolic processes essential for the life of the cell. While this is desirable to prevent infection, the action of the inorganic silver salts is indiscriminate and effects germs as well as healthy tissue. Specifically, patients treated with topical silver sulfadiazine have developed acute leukopenia, a condition in which the number of white blood cells (leukocytes) is abnormally low. The leukocyte counts in some of the patients who developed leukopenia were found to return to within normal limits within 48 to 72 hours after the discontinuation of silver sulfadiazine therapy. It has been recommended that daily leukocyte counts be done in burn patients being treated with silver sulfadiazine.

Accordingly, it is an object of the invention to provide a method of manufacturing a composition for treating skin lesions including burns which does not produce the unwanted side effects of burn treatment methods of the prior art.

Another object of the invention is to provide a method of manufacturing a composition for treating skin lesions which is easy to use and makes the application of dressings unnecessary.

Still another object of the present invention is to provide a method of manufacturing a composition for treating skin lesions which is easily tolerated by normal tissues, does not cause allergic reactions, is not absorbable in the tissues of the patient and is chemically neutral.

A further object of the invention is to provide a method of manufacturing a composition for treating skin lesions which permits the patient to move freely.

Another object of the invention is a method of manufacturing a composition for treating skin lesions which prevents infections in all open wounds.

Another object of the invention is to provide a method of manufacturing of composition for treating skin lesions which is useful in the application of skin grafts.

Another object of the invention is to provide a method of manufacturing of composition for treating skin lesions which facilitates the formation of scabs.

Another object of the invention is to provide a method of manufacturing of composition for treating skin lesions which provokes a high bactericidal effect against aerobic and anaerobic bacteria.

SUMMARY OF THE INVENTION

In accordance with the present invention, a composition for treating skin lesions is contemplated which includes metallic silver particles and an optional oxidizing agent disbursed within a carrier.

My invention further contemplates a method for treating skin lesions which includes applying to the lesion finely divided silver particles and an optional oxidizing agent disbursed within a carrier.

My invention resides in a method of manufacturing such a composition for such a method of treating skin lesions. The method comprises the steps of preparing a homogeneous wet mixture of a silver solution, clay and carbon powder; calcining the mixture (preferably at a temperature of about 700°–900° C. for about 0.5–5.0 hours) to produce a dry dispersion of finally divided silver particles in the clay; cooling the dispersion and grinding the same to a particle size capable of passing through a No. 200 sieve. The resultant powder may be packed in aerosol containers, hand dusters, or the like.

My invention further resides in the bactericidal composition produced by such method.

DETAILED DESCRIPTION OF THE PREFERRED EMBODIMENTS

The composition of the present invention is formed from finely divided metallic silver particles and an optional oxidizing agent dispersed within a carrier. The silver particles are preferably from 1 to 10 microns in size and form at least 3%, by weight, of the total composition. This particular silver particle size and range provides sufficient amount of particle surface area in contact with the lesion and yet the particles are not so small as to be impractical and expensive to manufacture and handle. In addition, while the metallic silver particles may constitute 3% of the composition, the composition has been found most effective when the metallic silver particles make up approximately 5%, by weight, of the total composition.

The oxidizing agent is used to cause the oxidation of the metallic silver particles and to produce oxygen to kill anaerobic bacteria. It is believed that upon oxidation, the silver particles generate silver oxide ions. These silver ions are a known antiseptic and germicide and kill the microbes which infect the lesion. While any suitable oxidizing agent may be used, benzoyl peroxide is preferred as it is a known bactericide and is commonly used in many acne preparations. The oxidizing agent should make up at least 1%, by weight, of the total composition and preferably should constitute approximately 1.5% of the composition. It will readily be appreciated that the oxidizing agent should be in a granular form so as to mix freely with the metallic silver particles in the carrier.

The carrier may be any inert filler in which the metallic silver particles and the oxidizing agent are randomly dispersed. The amount of carrier used will vary depending on the amount of silver particles and oxidizing agent used, but will generally be between 90 and 96% of the total composition. While any inert filler may be used, it is preferred than an absorbent inert powder such as kaolin or talc be used. Kaolin has been found most effective in the composition of the present invention as it absorbs moisture to dry the wound and is hemostatic, thereby facilitating scab formation. As a result, the loss of liquids, which is especially severe in burn patients, is avoided. The absorption of moisture from the lesion also eliminates fertile areas for bacterial growth. The kaolin or other inert powder will form part of the scab and is not absorbed into the normal tissues of the patient.

The composition described above further includes optionally an analgesic which is also dispersed within the carrier. The analgesic should constitute approximately 5%, by weight, of the total composition with the amount of carrier reduced accordingly. Any suitable analgesic may be used such as lidocaine hydrochloride.

In a preferred embodiment of the invention, the composition includes finely divided metallic silver particles ranging in size from 1 to 10 microns and forming approximately 5% of the total composition, together with benzoyl peroxide forming approximately 1.5% of the total composition, lidocaine hydrochloride forming approximately 5% of the composition and kaolin forming the remaining 88.5% of the composition. The silver particles, benzoyl peroxide and lidocaine hydrochloride should be uniformly distributed in the kaolin such that the composition is in a generally powdered form. The composition, as such, may be applied to lesions by simply dusting the lesion with the composition. The composition may also be contained in an aerosol spray can and sprayed onto the lesion. When the composition is used in this manner, any suitable propellant, such as freon, may be used. The composition is correctly applied to lesions by simply covering the lesion with the composition in its powder form. No other dressings are needed except in situations where interdigital separation is required. The composition thus applied will permit sufficient silver ion production. It will be readily appreciated that the application of the composition is quite simple and can be performed by doctor or patient after a minimum of instruction.

Because of its bactericidal properties, the composition of the invention may be used in dermo-epidermic wounds with infections and/or exudate, such as:

ACCIDENTS

Burns of different degrees, open wounds, dermal and epidermal skinning.

SURGERY (infected post-operative wounds)

Cholecystectomies, gastrectomies, laparotomies, appendectomies, (abcess, gangrene of the appendix), colostomies, fistulae, surgery involving contact with fecal matter, suture lines and scars infected by second or third intention.

RECONSTRUCTIVE SURGERY

Donor zones for free grafts.

PERIPHERAL VASCULAR SYSTEM

Sluggishly healing ulcers, pressure ulcers.

ORTHOPEDICS

Drying up of secretions due to friction or chafing.

DERMATOLOGY

Primary infections of the skin such as:
Impetigo (remove the scabs before applying the product)
Superficial folliculitis
Furunculosis Sycosis of the beard
Gangrenous Pyoderma.

SECONDARY SKIN INFECTIONS

Infected eczematous dermatitis
Purulent acne
Postulous psoriasis
Infected chafing
Bacterial infections on top of mycotic and viral infections
Sluggish ulcers
Eschars
Superficial ulcers
Decubitess and varicos ulcerations
Mycosis with secondary infection
Prevention of infections of surgical and traumatic wounds.

The composition of the invention is well tolerated by the patient's normal tissues and does not cause secondary effects or allergic phenomena. None of the substances making up the composition, both the active and the therapeutically inactive ones, provoke local or general sensitivity phenomena. The composition is chemically neutral and is not absorbable through the skin or the mucous membranes.

Because of the above-mentioned characteristics it is possible to use the composition in high and frequent dosages. The area of lesion and its general condition will indicate the amount to be applied. One or two applications daily are suggested, with application three times a day when there is abundant secretion. The composition should be used as follows:

1. Before applying the composition, the lesion should be cleaned with a sterile physiologic, isotonic solution to eliminate necrotic material.
2. If the solution is contained within a aerosol spray can, the can should be well shaken before each application in order to disburse all of the components of the composition, to assure a uniform spray application.
3. The spray can should be tilted slightly and spaced approximately 15 centimeters from the lesion. The composition should be applied to the lesion such that a thin layer of the composition covers the entire lesion. Spraying in a generally circular direction is recommended.

4. As the coldness of the propelling agent may cause pain, the stream of the spray should not be directed to one location for too long.

The novel bactericidal composition of the present invention is prepared by a process based on a reduction chemical reaction, which may be represented as follows:

$$2\ AgNO_3 + C \rightarrow CO_2 + 2\ Ag + 2\ NO_2$$

The reaction produces finely divided silver particles which may be carried by a carrier such as clay.

The novel method of preparing the bactericidal composition is initiated by preparing a wet homogeneous mixture of a silver solution, clay and carbon powder. The mixture is then calcined to produce a dry dispersion of finely divided silver particles in the clay. Finally, the dispersion is cooled and ground to a particle size capable of passing through a No. 200 sieve.

In forming the homogeneous wet mixture, the silver solution may employ an organic compound such as proteinic silver derivatives or inorganic silver salts such as silver nitrate, silver halides (for example, the chloride, iodide, bromide or fluoride salts) or other common silver precursors or silver-containing salts. Silver nitrate is greatly preferred because in the reduction chemical reaction indicated above, the disappearance of the nitrate may be used to monitor the progress of the chemical reaction. The silver solution is prepared by dissolving the silver compound in purified water, such as demineralized or distilled water. The concentration of the silver solution may vary widely without adversely affecting the method of the present invention.

The clay, which will be the carrier for the finely divided silver particles, is preferably kaolin, also known as "bolus alba" or "white clay". Prior to its introduction into the mixture, the clay may be heated at temperatures between about 100° and 800° C. to eliminate moisture therefrom. Lower temperatures require greater heating periods, and higher temperatures require briefer heating periods. This heating of the clay to eliminate its moisture enables one to utilize a known quantity of the clay. Without such a heating treatment the true amount of clay actually present in the "clay" used to form the wet mixture will vary considerably depending upon the moisture content of that "clay".

The carbon powder employed may be either vegetable or animal in origin and is preferably added as a powder composed of finely divided particles.

The components of the wet mixture may be added in any order. Preferably the silver solution and clay are combined first, with the carbon powder being added thereto with continuous mixing until a homogeneous wet mixture is obtained.

After the homogeneous wet mixture is formed, it is calcined to produce a dry dispersion of finely divided silver particles in the clay. Calcining may be performed in a furnace at a temperature of about 700°–900° C. for a period of 0.5°–5.0 hours. The period of time required to produce the free silver particles may be monitored by techniques well known to those in the chemical arts. For example, when the silver solution is a solution of silver nitrate, the nitrate disappearance may be monitored, the disappearance indicating that the chemical reaction has been completed.

The resultant product, that is, the dry dispersion of finely divided silver particles in clay, is then slowly cooled. If desired, additional ingredients may be added at this time such as benzoyl peroxide and/or lidocaine hydrochloride, with the amount of clay being reduced accordingly. The benzoyl peroxide may be used in an amount of 1.5±0.5% by weight and the lidocaine hydrochloride may be used in an amount of 4–5% by weight. The use of these additives is, however, optional and not necessary for the functioning of the present invention.

The cooled dispersion, which may contain the aforementioned optional additives or others, is then ground to a particle size capable of passing through a No. 200 sieve, using grinding procedures well recognized in the material processing art (for example, a ball grinder). The aforementioned optional additives (or others) may be added after grinding, rather than before, provided that they do not exceed the particle size designated above. The ground powder is then packed according to the intended application technique, for example in an aerosol container, in a package for hand dusters, etc.

In a preferred embodiment of the method, the homogeneous wet mixture is prepared by dissolving about 8.5 parts by weight of silver nitrate powder in distilled water to obtain an aqueous solution. Separately, about 91.5 parts by weight of kaolin is heated to a completely dried product and then mixed with the silver nitrate solution to form a wet mixture. Finely divided carbon is added, with continuous mixing, in order to obtain a homogeneous wet mixture. The homogeneous wet mixture is then calcined at a temperature of abut 800° C. for about 0.5–5.0 hours to produce a dry powder. The dry powder is then slowly cooled and ground in a ball grinder until the powder has a particle size capable of passing through a No. 200 sieve.

The ratio of the silver solution to the clay may be varied considerably in order to provide a desired concentration of silver in the carrier, the same varying with the type of bacterial infection, the site of the injury, etc. The amount of carbon powder employed in the wet mixture is not a critical feature of the present invention, although generally carbon levels in excess of the stoichiometric requirement (according to the above-indicated reduction chemical reaction) are preferred.

In order to evaluate the composition and method of the present invention, a series of clinical studies were carried out.

EXAMPLE 1

In the General Surgery Service of the Centro Hospitalario "20 de Noviembre" located in Mexico City, Mexico, fourteen patients of both sexes were treated, nine women and five men between ten and seventy-five years old, with an average age of thirty five years. The patients had wounds infected between the 5th and 6th post-operative day (appendectomy, gastretomies, cholecystectomies, inguinal hernias, umbilica hernias, exploratory laparatomies, etc.).

In all the cases, a control of the infection process was run through the laboratory and clinical methods. Before the application of the composition of the invention, a bacteriological examination was made of the wound secretions through cultures in liquid media with later staining by Gram Method. On the 5th and 10th day of treatment, a new bacterial examination of the secretions was performed (culture). The white blood cells were also studied before, during and after treatment.

The composition of the invention was applied to all patients' wounds after cleaning each wound with an isotonic, physiological solution, using sponges to extract necrotic areas. This procedure was carried out twice a day.

The composition was contained in an aerosol can which was shaken first so as to achieve a homogeneous spray. The composition was applied at a distance of 10 to 15 centimeters from the lesion in such a way that the composition was spread over the whole wound. All patients were treated in the same manner, without considering the degree of depth or extension of the lesion.

A group of eleven patients were administered only the composition on their wounds. The other group of three patients, also treated with the composition, had previously been administered systemic antibiotics and had other substances applied to lesions.

RESULTS

1. The germs found in the first culture (before the application of the composition) of the wound secretions were:
(a) Salmonella: 2 cases
(b) Klebsiella aerobacter: 1 case
(c) Proteus mirabilis: 1 case
(d) Staphylococci: 1 case
(e) Escherichia coli: 8 cases.
Infection with Escherichia coli was the most frequent.

2. All the patients treated with only the composition of the invention (eleven patients) recovered satisfactorily, with the response in both sexes and in the different ages being similar. The type of germ found initially (first culture) was also not an important factor. The wound secretions became very scarce with twice daily applications of the composition. The cultures performed after after treatment found no trace of any of the germs.

The post-operative wounds of two of the patients were sutured when they were free of all infection.

In general, recovery was seen in all the cases with the appearance of granulation yolks between the 4th and 5th day, and complete healing between the 8th and 14th days.

3. Three of the cases had products or substances applied locally on the wounds, such as: Furacin, Benzal, oxigenated water, merthiolate, Lassar paste, Bacitracin or Kanamicine, etc., as well as being treated with systemic antibiotics. In these cases, healing was no more rapid than in the group treated with the composition alone.

COMMENTS

It was observed that the composition was an efficient medication for treatment of post-operative wound infections. The composition was tolerated well, secondary effects and allergic phenomena did not occur and in none of the cases was it necessary to use antiseptic substances before applying the composition. The wounds were cleaned only with a physiologic solution.

The compositions formed a protective layer that isolated the wounds from the environment, making the application of dressings unnecessary. The product required shaking before being applied, because on occasions the substances did not mix satisfactorily.

CONCLUSIONS

The fourteen patients treated with the composition were of different ages and sexes, and each had post-operative wound infections. The majority were treated only with the composition and the others were also treated with other topical products and systemic antibiotics.

Cultures of the wound secretions were done in all the patients before, during and after the treatment. Infection in most of the patients was due to escherichia coli, and in general, cicatrization (heal by formation of a scar) occurred between the 8th and 14th days.

EXAMPLE II

Eighty patients were studied in the Hospital de Traumatologia de la Villa (La Villa Traumatology Hospital) in Mexico City, Mexico, in order to evaluate the composition of the invention. Only 53 of the patients were treated with the composition, the remaining 27 serving as controls.

Of the 53 treated with the composition, 24 patients presented first and second degree burns and 26 patients had dermal-epidermal skinning on different parts of the body.

On 24 of the patients having first and second degree burns, the composition was applied immediately over bleeding areas. Scabs formed which were maintained free of secretions due to the absorbent action of the kaolin. When the scabs, which acted as physiologic dressings, flaked off, epithelialized zones with normal characteristics were observed.

In three cases in which medium thickness free grafts were applied, in-layer hemorrhaging impeded fixation to the site of the lesion. Once the in-layer hemorrhaging was restrained by compression with dressings and warm physiological solution, the composition was applied, obtaining drying of the wounds during the cicatrization period.

In twenty-six patients with dermal/epidermal skinning (on different parts of the body), the composition was applied and no modification was observed in pain and bleeding. These lesions had an uncomplicated cicatrizing (heal with scar) evolution. In three patients with wounds infected because their treatment was instituted late, treatment with the composition was supplemented with antibiotics, and a notable reduction was seen in seropurulent secretions.

TABLE A

|  | Cases | Extension | Evolution to cicatrization | Infection | Treatment |
| --- | --- | --- | --- | --- | --- |
| TREATMENT WITH COMPOSITION | | | | | |
| Burns | 24 | 7% to 15% body surface | 8–13 days | 0 cases | 11 with baths, 6 free grafts |
| Donor areas | 3 | 3% to 5% | 8 days | 0 cases | — |
| Dermal/Epidermal skinning | 26 | 5% to 20% | 7–15 days | 0 cases | 3 antibiotics parental route |
| CONTROL CASES | | | | | |
| Burns | 13 | 10 to 20% body surface | 12–25 days | 5 cases | Open method mechanical wash |

TABLE A-continued

| | Cases | Extension | Evolution to cicatrization | Infection | Treatment |
|---|---|---|---|---|---|
| Donor areas | 6 | 5% to 10% body surface | 8–14 days | 1 case | Furazone dressing |
| Dermal/Epidermal skinning | 8 | 5% to 20% body surface | 8–10 days | 3 cases | Mechanical wash |

The bacteriological examination by the Gram stain method and culture in liquid media identified: gram negative bacilli, streptococci, staphylococci and diplococci.

Of the 27 control cases, 19 were patients with first and second degree burns and the remaining eight had dermal/epidermal skinning on different parts of the body. Thirteen patients with first and second degree burns were treated with the open method and mechanical wash, infection appearing in five cases.

Six cases of donor areas (skin grafts) were covered with nitrofurazone dressings, infection being found in one case.

Eight patients with dermal/epidermal skinning on different parts of the body were treated with mechanical wash, using water and soap and applications of nitrofurazone dressings. Infections were found in three cases (See Table A).

CONCLUSIONS

1. The composition of the invention is easily tolerated by the tissues, does not cause allergic reactions, is not absorbable and is chemically neutral.
2. The benefits obtained with the composition are as follows:
   (a) the proliferation of bacteria is inhibited as there are no secretions providing an appropriate medium for proliferation;
   (b) the formation of a physiological dressing (with the composition) diminishes the cicatrization period, since exterior contamination is avoided; the formation of a scab isolates the lesion from the exterior environment, avoiding new contamination and acting as a physiological dressing.

EXAMPLE III

This evaluation was carried out at the Burns Unit of the Central Emergencies Hospital "Dr. Ruben Lenero" in Mexico City, Mexico.

CLINICAL ASPECTS

A group of 139 patients was studied between June, 1980 and June 1981. Their ages ranged between 5 and 70. Burned body surfaces ranged between 5 and 8% and encompassed the three classically accepted degrees.

This group was compared with another that had been hospitalized previously and treated by the exposed method. This group was carefully chosen in order to find the closest possible similarity with the patients being studied, taking into account the following factors: age, extension and depth of the burn and topography.

Treatment for both groups was quite similar in respect to the systemic treatment (in those patients who required it) for shock caused by trauma.

The management of each case was always directed to maintaining, wherever possible, the figures considered as "normal" in parameters such as: blood pressure, central venous pressure, body temperature, diuresis, serum electrolytes, etc. Blood, colloids, saline and glucose solutions, electrolytes and medicinal drugs such as: Digitalis, corticoids, vasomotors, antibiotics, etc. were all administered in accordance with the usually recommended doses, conditioned to the patient's response.

In all cases routine laboratory tests were made such as: complete blood count, blood chemistry, general urinalysis measurement of electrolytes, and in some, glutamic-oxalecetic and pyruvic transaminase. Blood and lesion exudate cultures were also made, with their corresponding antibiograms and boisies of the lesions and surrounding tissues made whenever deemed necessary. In the patients of the study group who died, special attention was paid during autopsy to a comprehensive study of the reticuloendothelial, conjunctive tissues and the parenchyma of the organs, in an attempt to find silver deposits.

Once the general guidelines for the intensive therapy were established, we directed out attention to the local treatment of the lesions. After sedation and analgesia of the patient, a profuse washing out of the lesions was carefully performed using a sterile saline solution and voluminous swabs made of soft cotton, in order to minimize pain. Any remaining debris and clothing were detached if possible, and blisters were cut away and necrosed to their depth to obtain a better impregnation of the composition. The composition was applied to the lesions and to the surrounding skin for a distance of about 1½ inches. The patient's burned surfaces were then left exposed.

This treatment was performed at time intervals not greater than 24 hours. We directed our attention mainly to changes that may possibly take place with respect to pain, degree of humidity, presence or absence of exudates, edema, progress in the formation of scabs, etc. This method permitted the direct observation of the condition of the burned surfaces which are totally exposed with the exception of hands. Hands are often covered with bulky bandages to insure an interdigital separation and to place the hand in a functional position.

When inspecting the lesions daily, the portions of the sloughs that were detached were cut away and the composition was again applied. This operation was repeated until a complete debridgement of the sloughs was observed. In the case of first and second degree superficial and deep burns, this was accomplished without using any other procedure. In the cases in which the lesion was deeper, it was observed that on an average, 15 to 17 days of treatment was sufficient ot permit an exeresis of the slough using bath-sessions and in some cases even a debridement under general anesthesia in the operating room.

In the raw areas obtained after debridement and on which skin grafts were necessary, the open method was changed to a closed one. The lesions were covered with wet dressings, dipped in saline solutions, suppressing application of the composition. In these cases, it was observed that granulation tissue developed more rapidly (usually after the third bath-treatment). As a result, it was possible to consider the immediate application of skin grafts, (an average of 15 days).

In respect to pain, it was noted that in a few minutes (5) after application of the composition, the patients admitted that they were more comfortable. This is difficult to evaluate perse, due to its subjective nature. However, most of the patients, required less analgesic medication.

The presence of exudates, degree of humidity, edema, etc. always diminished considerably after application of the product.

that of acute abdomen, and the patient died while undergoing an exploratory laparatomy.

In another case, shock due to aderenal failure was diagnosed. There was no response to therapy and at autopsy, abundant hemorrhagic points were found in the adrenal capsules.

In a third case, a post-mortem diagnosis was cerebro vascular hemorrhage.

In all cases of this group, a purposeful search was carried out for signs of silver inclusion in connective tissue and the reticulo-endothelial system, but none was found.

TABLE B

| PERCENTAGE OF BURNS | EXPOSED METHOD | | COMPARATIVE INDICES OF MORTALITY | | COMPOSITION | |
|---|---|---|---|---|---|---|
| | No. of patients | No. of deaths | | | No. of patients | No. of deaths |
| 0–20% | 54 | 0 | 0% | 0% | 60 | 0 |
| 21–35% | 63 | 3 | 4.77% | 0% | 57 | 0 |
| 36–50% | 19 | 10 | 52.60% | 15% | 20 | 3 |
| 51–70% | 20 | 20 | 100.0% | 85% | 20 | 17 |
| 71–80% | 13 | 13 | 100.0% | 100% | 12 | 12 |
| TOTAL: | 169 | 46 | | | 169 | 32 |

RESULTS

Mortality:

Comparative indices of mortality are found in Table B. The composition was applied on sixty patients whose total burned body surface was less than 21%. Comparative or control groups were made up of patients treated by the exposed method and having burn lesions that were similar in extension, depth and topography to the above group. There were no deaths in either group.

There were no deaths either in another group treated with the composition who had burned body surfaces ranging from 21 to 25%. In a comparative group treated with the exposed method, there were three deaths in sixty-three cases, equivalent to a mortality rate of 4.77%.

Twenty patients with burned areas from 26 to 50% were treated with the composition. Three of them died, giving a mortality rate of 15%. Of nineteen comparable patients treated with the exposed method, ten died, giving a mortality rate of 52.6%.

Of twenty patients treated with the exposed method, with burns covering 51 to 70% of the body surface, all twenty died, giving a mortality rate of 100%. Of ten patients treated with the composition, having the same percentage of burned area, 17 died, corresponding to a mortality rate of 85%.

Of thirteen patients treated with the exposed method and twelve patients with the composition, each with burns from 71 to 90% of body surface, all died in both groups.

CAUSES OF DEATH

In all deaths (46 treated with the exposed method and 32 with the composition), signs of infection prior to death were found, such as: fever, profuse sweating, delirium, hypotension, etc. At autopsy, pneumonia was found.

In the group treated with the composition, there were three deaths in which the main cause of death was something other than sepsis (blood poisoning) even when this was present. In one case, multiple ulcers were found in the stomach and duodenum (curling), some of them perforated. The clinical picture prior to death was In the group treated by the exposed method, even when no findings showed death attributable to the infectious shock, it was considered that the septic picture was so severe as to cause the death of these patients perse. (See Table C).

TABLE C

| TREATMENT | Number of Patient Deaths Caused by Septisemia | Number of Times When Septisemia Was Diagnosed |
|---|---|---|
| EXPOSED METHOD | 46 | 73–43% |
| COMPOSITION | 29 | 52–30% |

Number of times when septicemia was diagnosed:

Whenever a diagnosis of septicemia was made, it was based on the clinical picture presented by the patient. In most, although not all, of these cases the blood culture was positive for bacteria. At other times, positive blood cultures were obtained without a clinical picture of septicemia; these cases were not included. Lastly, at times the patient presented more than one picture of septicemia.

In patients treated by the open method, septicemia was diagnosed 73 times, equivalent to 43%. In groups treated with the composition, septicemia was diagnosed on fifty-two occasions which is equivalent to 30%. (See Table C).

Average hospitalization time:

In order to estimate this time, only those patients who survived were counted; that is, 123 of the group treated by the open method and 137 of the group treated with composition. In the first group the average hospitalization time was 50 days, while in the second group it was 43. (See Table D).

Average time for total elimination of sloughing:

It was attempted to eliminate sloughing by means of bath-sessions as soon as the slough began to detach from the periphery, cutting away only those parts that had become separated. Where the slough was firmly adhered to the deep layers for a period of over 20 days and the patient's condition warranted it, the slough was removed surgically.

TABLE D

| TYPES OF TREATMENT | AVERAGE HOSTITALIZATION TIME | | AVERAGE TIME FOR TIME ELIMINATION OF SLOUGHING |
|---|---|---|---|
| | No. of Patients | No. of Days | |
| EXPOSED METHOD | 123 | 50 | 20 days |
| COMPOSITION | 137 | 43 | 17 days |

Note: Only those patients who survived were counted.

TABLE E

| TYPE OF TREATMENT | TOTAL NO. OF BLOOD CULTURES | POSITIVE BLOOD CULTURES | *PSEUDOMONA AUREOGINOSA* | *AEROBACTER KLEBSIELLA* | *STAPHYLOCOCCUS AUREUS* | ANOTHER COCCUS GRAM NEGATIVE |
|---|---|---|---|---|---|---|
| EXPOSED METHOD | 350 | 212 (62%) | 100 (47%) | 83 (39%) | 74 (34%) | 13 (6.1%) |
| COMPOSITION | 507 | 238 (48%) | 126 (52%) | 40 (16%) | 11 (4.6%) | 23 (9.6%) |

In the group treated by open method, the average time needed for the total removal of the slough was 20 days. In the group treated with the composition, the average time for total removal of the slough was reduced to 17 days.

Appearance of debrided areas:

In patients treated with the composition, the appearance of the deep areas, once the slough was debrided, was rather clean and granulation more homogenous; this permitted the application of grafts sooner. Additionally, a greater percentage of skin growing underneath the scabs was observed.

Fewer washings prior to the application of skin grafts were necessary - an average of three in those patients treated with the composition as opposed to five in those treated by the open method.

Blood cultures:

In the group treated by the open method, 350 blood cultures were made, of which 212 (62%) were positive for the presence of bacteria. Of these, 100 (47%) developed Pseudomona aureoginosa; in 83 (39%) Aerobacter klebsiella was found; in 74 cultures (34%) Staphylococcus Aureus was grown, and in 13 (6.1%) other Gram negative cocci were found. (See Table E).

Culture from wound:

169 cultures were developed from the wound in the group treated by open method, of which 123 (72%) developed germs. Of these 123 positive cultures, 73 (59%) grew Pseudomona aureoginosa; 40 (32%) Aerobacter klebsiella and 51 (41%) Staphylococcus aureus. (See Table F).

the body (there were no deaths in either the group treated with the composition or the comparable group treated by the open method). However, those patients treated with the composition were more comfortable. Patients treated by the open method often feel cheated when they see that their lesions are not touched (even when the need to do this is explained). This fact causes a certain degree of depression which perhaps interferes to some extent with the patient's recovery. It is highly probable that this problem has been overcome in the group where the patients were treated with the composition on a daily basis. Naturally, a rapid evolution towards healing is not only the product of psychological conditioning, caused by the application of the composition, since the number of cultures, days with temperature (fever) and appearance of the lesions show differences attributable only to a lesser proliferation of bacteria at the site of the lesion.

In the groups where the burns covered from 71 to 80% of body surface, no appreciable differences were found between the group treated with the composition and the comparable group treated by the "open method" (all patients died). However, it is to be observed that in the group treated with the composition, there were two deaths in which the determining cause was in one case, adrenal failure, and in the other, a cerebro vascular accident. It should be noted that the time of survival was greater in the group treated with the composition.

EXAMPLE IV

Presentation of gas - gangrene

This evaluation was carried out with the consideration that the anaerobic causative agent of gas-gangrene has a more or less close symbiosis with aerobic organisms. This symbiosis accelerates the lethal course of the infection. A mixed infection with streptococci leads to an especially poor prognosis.

The activity of the causative agent has been thoroughly tested on over 400 guinea pigs with 6 different anaerobic strains, a highly virulent staphylococcus, and two streptococcus strains. The control animals in every case developed severe cases of gas-gangrene typical of

TABLE F

| KIND OF TREATMENT | BLOOD CULTURES | POSITIVE BLOOD CULTURES | *PSEUDOMONA AUREOGINOSA* | *AEROBACTER KLEBSIELLA* | *STAPHYLOCOCCUS AUREUS* |
|---|---|---|---|---|---|
| EXPOSED METHOD | 169 | 129 (72%) | 73 (59%) | 40 (32%) | 51 (41%) |
| COMPOSITION | 230 | 97 (42%) | 52 (53%) | 33 (34%) | 15 (15.4%) |

CONCLUSIONS

There was no difference in mortality rate in the groups that had burns that covered as much as 20% of the particular pathogen used, and died within 8-10 hours of being inoculated with 0.2 ml of an anaerobic liver-liver bouillon.

TABLE G

| Type of Infection | No. Exp. Animals | Treatment After Infection immediately | after 2 hrs. | after 5 hrs. | after 7/12 hrs. | Survivors total | % |
|---|---|---|---|---|---|---|---|
| Mono-infection with 4 gas gangrene strains | (a) 48 | 12/12 | 12/12 | 7/12 | 5$^i$/12 | 36/48 | 75 |
| | (b) 48 | 0/12 | 0/12 | 0/12 | 0/12 | 0/48 | 0 |
| Gangrenous tissue implanted | (a) 8 | 2/2 | 2/2 | 1/2 | 0$^{ii}$/2 | 5/8 | 62.5 |
| | (b) 8 | 0/2 | 0/2 | 0/2 | 0/2 | 0/8 | 0 |
| Anaerobic mixed culture | (a) 12 | 3/3 | 3/3 | 1$^{iii}$/3 | 2/3 | 9/12 | 75 |
| | (b) 12 | 0/3 | 0/3 | 0/3 | 0/3 | 0/12 | 0 |
| Anaerobic aerobic mixed culture | (a) 12 | 3/3 | 3/3 | 2/3 | 1/3 | 9/12 | 75 |
| | (b) 12 | 0/3 | 0/3 | 0/3 | 0/3 | 0/12 | 0 |

(a) = Animals treated with composition
(b) = Control animals
Numerator = surviving animals
Denominator = Number of experimental animals
i = 5 animals died more than 48 hrs. after infection
ii = 1 animal died more 48 hrs after infection
iii = 1 animal died more than 48 hrs. after infection The aerobic infections were made by infecting a wound made in the musculature of the back with 0.2 ml of a bouillon culture of the pathogen, neglecting all sterile precautions. The number of experimental animals was 12.

Treatment with the composition of the invention was carried out immediately, two and four hours after the infection and was repeated every two and four hours respectively. The composition (200 mg) was blown into the wound with a powder blower. The control animals developed abscesses and a smeary festering wound crust. In the 12 treated animals, all wounds, with the exception of the cases in which pus had formed prior to treatment, healed quickly. The animal in which pus had formed prior to treatment, did respond to a second treatment and developed a normal wound.

For summarized results of tests of anaerobic strains see Table G.

Implantation of a lentil-sized highly infected piece of tissue from a human gas-gangrene infection yielded the same survival figures. Experiments wherein mixed anaerobic-aerobic flora of all strains were used, yielded similar results.

After numerous experiments demonstrated the preferable effect of the composition, a blank comparison test was carried out with four other wound powders (designated: A, B, C and D). The results of the test on 54 animals (treatment immediately, four and seven and one-half hours after infection) are summarized as follows:

TABLE H

| | Tested Wound Powder | | | | |
|---|---|---|---|---|---|
| Control | A | B | C | D | Composition |
| 0/9 | 1/9 | 0/9 | 0/9 | 1/9 | 6/9 |
| | | | Survivors | | |
| 0% | 11% | 0% | 0% | 11% | 66% |

Numerator = Surviving animals
Denominators = Number of experimental animals

The difference in survival between the group treated with the composition and the groups treated with the wound powders A and D was 66% against 11% and is statistically significant.

A tolerance test on nine animals for each powder using a three-fold dosage of the usual quantity of A, B, C, D and the composition yielded the following results on 45 animals:

TABLE I

| Wound Powder: | A | B | C | D | Composition |
|---|---|---|---|---|---|
| Animals: 45 | 0/9 | 1/9 | 3/9 | 4/9 | 9/9 |
| Survivors: | 0% | 11% | 33% | 45% | 100% |

Numerator = Surviving animals
Denominator = Number of experimental animals

The difference in survival between the group treated with the composition and the group treated with wound powder D was 100% against 43% and is statistically significant. The same holds for the smaller values of 0%, 11% and 33%.

The investigations with the various wound powders were then carried out with a series of test using mixed anaerobicaerobic floras and again, favorable results were obtained with the composition. See Table J.

TABLE J

| Wound Powder | I | II | III | Controls |
|---|---|---|---|---|
| A | Anaerobic-aerobic flora on dried stair dust<br><br>Treatment: 7 hours after infection<br><br>1/5 Deaths of control group animals | One loopful of mixed anaerobic-aerobic culture flora<br><br>Treatment: 7 hours after infection<br><br>1/5 Deaths of control group animals | Three loopfuls of mixed anaerobic-aerobic culture flora<br><br>Treatment: 7 hours after infection<br><br>0/5 All died 10 to 14 hours after | All died 7 to 10 hours after |

TABLE J-continued

| | I | II | III | Controls |
|---|---|---|---|---|
| | | | infection | infection |
| B | 0/5 One animal died after 76 hours. Two animals died after 80 hours. | 0/5 Four animals died after 20 hours. One animal died after 32 hours. | 0/5 All died 10 to 18 hours after infection. | |
| C | 0/5 One animal died after 144 hours. One animal died after 164 hours. | 1/5 | 0/5 Two died 7 to 8 hours after infection. Three died after infection. | |
| D | 0/5 | Not tested | 0/5 Three died 7 to 8 hours after infection. Two died 11 hours after infection. | |
| Composition | 4/5 | 4/5 | 1/5 Four died more than 48 hours after infection. One survivor. | |

Since the deaths of all animals, including the control group in group I, Table J, occurred relatively late, the infecting dosage was considerably increased in two further tests, II and III.

Despite the more rigorous experimental conditions which were clearly indicated by the speed with which the control group animals succumbed, 80% of the animals treated with the composition survived against 20% of the animals treated with other wound powders A, B and C.

With a triple dosage (no animals were expected to survive), it was possible to determine how effective the various wound powders would be in delaying death. Animals treated with the composition demonstrated a decided inhibition in the course of the infection and, despite all expectations, one animal survived this massive infection. In addition, the animals treated with the composition survived longer.

Finally, experiment I was repeated as a double blank test. The test was discontinued after 30 hours, after the superiority of the composition was clearly demonstrated. See Table K.

TABLE K

| Blank Preparation | 1. Series | 2. Series |
|---|---|---|
| A | 2/5 | 3/5 |
| B | 5/5 | 5/5 |
| C | 2/5 | 3/5 |
| D | 5/5 | 5/5 |
| Controls | 1/5 | 1/5 |

Numerator = Surviving animals
Denominator = Number of experimental animals

On the basis of these experimental results, it appears that the recommended use of the composition as a prophylactic and therapeutic in seriously contaminated wounds, especially in cases of catastrophe in which early surgical treatment is doubtful, is justified.

CONCLUSIONS

In exhaustive animal experiments, guinea pigs were infected by insertion of various strains of gas-bacilly, mixed cultures into seriously damaged muscle tissue.

Treatment with the composition took place immediately after infection, or after two, five and seven and one-half hours. Approximately 62.5% to 75% of the infected animals who were treated seven and one-half hours after infection, survived. Comparison experiments with other wound powders, carried out in part in parallel (double) blank tests, clearly demonstrated the significant superiority of the composition.

In extensive pharmacological tests, a dosage of the composition which was triple that normally used, did not damage the animals, thus confirming excellent tolerance. The impossibility of obtaining surgical treatment within the time limit (three and one-half hours) in large catastrophes bears out the usefulness of the prophylactic and chemotherapeutic properties of the composition of the invention.

As will be readily apparent to those skilled in the art, the invention may be used in other specific forms or for other purposes without departing from its spirit or central characteristics. The present embodiments are therefore to be considered as illustrative and not restrictive, the scope of the invention being indicated by the claims rather than by the foregoing description, and all embodiments which come within the range of the equivalence of the claims are intended to be embraced.

What we claim is:

1. A method of preparing a bactericidal composition comprising finely divided silver particles carried by clay, comprising the steps of:
   (A) preparing a homogeneous wet mixture of a silver solution, clay, and carbon powder;
   (B) calcining the mixture to produce a dry dispersion of finely divided silver particles in the clay, the silver particles constituting at least 3% by weight of the dispersion;
   (C) cooling the dispersion and grinding the same.

2. The method of claim 1 wherein said silver solution is a silver salt solution.

3. The method of claim 2 wherein said silver salt solution is a solution of silver nitrate.

4. The method of claim 3 wherein said silver nitrate is dissolved in purified water.

5. The method of claim 1 wherein the clay is kaolin.

6. The method of claim 5 wherein the clay, prior to its introduction into the mixture, is heated to eliminate substantially all moisture therefrom.

7. The method of claim 6 wherein the clay is heated at a temperature of about 100°–800° C.

8. The method of claim 1 wherein in Step (A) the silver solution is mixed with dry clay in order to obtain a wet mixture, and then the carbon powder is added with mixing to form a homogenous wet mixture.

9. The method of claim 1 wherein in Step (A) the silver solution is mixed with moist clay and carbon powder.

10. The method of claim 1 wherein the silver solution is a silver nitrate solution, and the mixture is calcined in Step (C) until the presence of nitrates in the mixture is no longer detectable.

11. The method of claim 1 wherein the ground dispersion is mixed with active ingredients selected from the group consisting of benzoyl peroxide and lidocaine hydrochloride.

12. The method of claim 1 wherein the mixture is calcined at a temperature of about 700°–900° C. for about 0.5–5.0 hours.

13. A method of preparing a bactericidal composition comprising finely divided silver particles carried by a kaolin carrier, comprising the steps of:
 (A) preparing a homogeneous wet mixture of an aqueous silver nitrate solution, kaolin, and carbon powder;
 (B) calcining the mixture at 700°–900° C. for about 0.5–5.0 hours to produce a dry dispersion of finely divided silver particles in the kaolin, the silver particles constituting at least 3% by weight of the dispersion;
 (C) cooling the dispersion and grinding the same.

* * * * *